United States Patent
Luoma, II

(10) Patent No.: US 7,458,483 B2
(45) Date of Patent: Dec. 2, 2008

(54) ASSAY TESTING DIAGNOSTIC ANALYZER

(75) Inventor: Robert Paul Luoma, II, Highland Village, TX (US)

(73) Assignee: Abbott Laboratories, Inc., Abbott Park, IL (US)

(*) Notice: Subject to any disclaimer, the term of this patent is extended or adjusted under 35 U.S.C. 154(b) by 553 days.

(21) Appl. No.: 10/614,485

(22) Filed: Jul. 7, 2003

(65) Prior Publication Data

US 2004/0134750 A1    Jul. 15, 2004

Related U.S. Application Data

(63) Continuation-in-part of application No. 09/840,960, filed on Apr. 24, 2001, now Pat. No. 6,588,625.

(51) Int. Cl.
*G07F 11/00* (2006.01)
(52) U.S. Cl. .................. 221/7; 221/9; 221/13; 221/92; 221/123; 422/64; 422/65
(58) Field of Classification Search .................. 221/9, 221/13, 7, 92, 123, 124, 129; 422/65, 67, 422/63, 64, 66
See application file for complete search history.

(56) References Cited

U.S. PATENT DOCUMENTS

| | | | |
|---|---|---|---|
| 3,832,135 | A | 8/1974 | Drozdowski et al. |
| 3,985,507 | A | 10/1976 | Litz et al. |
| 4,077,444 | A | 3/1978 | Gilson et al. |
| RE30,627 | E | 5/1981 | Bagshawe et al. |
| 4,276,258 | A | 6/1981 | Ginsberg et al. |
| 4,299,796 | A | 11/1981 | Hogen Esch |
| 4,363,782 | A | 12/1982 | Yamashita |
| 4,501,164 | A | 2/1985 | Stockdale et al. |
| 4,582,990 | A | 4/1986 | Stevens |
| 4,676,951 | A | 6/1987 | Armes et al. |
| 4,678,752 | A | 7/1987 | Thorne et al. |
| 4,774,055 | A | 9/1988 | Wakatake et al. |

(Continued)

FOREIGN PATENT DOCUMENTS

EP    0 435 481 B1    7/1991

(Continued)

OTHER PUBLICATIONS

Extended European Search Report.

*Primary Examiner*—David H. Bollinger
(74) *Attorney, Agent, or Firm*—David L. Weinstein

(57) ABSTRACT

A diagnostic system with a handling system that has a loading bay to receive and hold a plurality of carriers. An identification device is configured to identify an identifying feature of the carriers to determine the type of contents loaded on each carrier. A transporter transports the carriers from the loading bay to a first or second location depending on the determined type of contents on each carrier. The transporter has random access to the plurality of carriers in the loading bay. A diagnostic process is conducted using the contents. A carrier, such a for reagents, has one or more holding portions, at least one of which can be moved or rotated with respect to the body of the carrier for mixing or stirring the contents of a container coupled therewith. Also, a retention member can be associated with a positioning device, such as a carousel, to lock and unlock the carrier with respect thereto.

11 Claims, 14 Drawing Sheets

U.S. PATENT DOCUMENTS

| | | | |
|---|---|---|---|
| 4,844,868 A | 7/1989 | Bokugawa | |
| 4,848,917 A | 7/1989 | Benin et al. | |
| 4,906,432 A | 3/1990 | Geiselman | |
| 4,931,402 A | 6/1990 | Abplanalp | |
| 4,965,049 A | 10/1990 | Lillig et al. | |
| 5,071,625 A | 12/1991 | Kelln et al. | |
| 5,087,423 A | 2/1992 | Ishibashi | |
| 5,122,342 A * | 6/1992 | McCulloch et al. | 422/65 |
| 5,163,802 A | 11/1992 | Poinelli | |
| 5,244,633 A | 9/1993 | Jakubowicz et al. | |
| 5,260,872 A | 11/1993 | Copeland et al. | |
| 5,266,272 A | 11/1993 | Griner et al. | |
| 5,314,825 A | 5/1994 | Weyrauch et al. | |
| 5,320,809 A | 6/1994 | Dunn et al. | |
| 5,324,481 A * | 6/1994 | Dunn et al. | 422/64 |
| 5,332,549 A | 7/1994 | MacIndoe, Jr. | |
| 5,380,487 A | 1/1995 | Choperena et al. | |
| 5,483,843 A | 1/1996 | Miller et al. | |
| 5,575,976 A | 11/1996 | Choperena et al. | |
| 5,591,642 A | 1/1997 | Jones | |
| 5,601,783 A | 2/1997 | Breeser et al. | |
| 5,658,799 A | 8/1997 | Choperena et al. | |
| 5,665,309 A | 9/1997 | Champseix et al. | |
| 5,681,530 A | 10/1997 | Kuster et al. | |
| 5,693,292 A | 12/1997 | Choperena et al. | |
| 5,736,102 A | 4/1998 | Seaton et al. | |
| 5,750,074 A | 5/1998 | Katzman et al. | |
| 5,795,784 A | 8/1998 | Arnquist et al. | |
| 5,853,667 A | 12/1998 | Seaton et al. | |
| 5,876,670 A | 3/1999 | Mitsumaki et al. | |
| 5,882,596 A | 3/1999 | Breeser et al. | |
| 5,972,295 A | 10/1999 | Hanawa et al. | |
| 6,056,921 A | 5/2000 | Rao et al. | |
| 6,060,022 A | 5/2000 | Pang et al. | |
| 6,071,477 A | 6/2000 | Auclair et al. | |
| 6,335,166 B1 | 1/2002 | Ammann et al. | |
| 6,358,472 B1 | 3/2002 | DeYoung et al. | |
| 6,890,485 B1 * | 5/2005 | Stylli et al. | 422/68.1 |
| 7,407,627 B1 | 8/2008 | Rosenberg et al. | |
| 2002/0155590 A1 | 10/2002 | Gebrian et al. | |
| 2002/0169518 A1 | 11/2002 | Luoma, II et al. | |
| 2003/0054542 A1 | 3/2003 | Burns et al. | |

FOREIGN PATENT DOCUMENTS

| | | |
|---|---|---|
| EP | 0 471 981 B1 | 2/1992 |
| EP | 0 502 638 B1 | 9/1992 |
| EP | 0 525 577 B1 | 2/1993 |
| EP | 0867724 A2 | 9/1998 |
| EP | 0979999 A2 | 2/2000 |
| JP | 62098262 | 5/1987 |
| JP | 01-250759 | 10/1989 |
| JP | 03183957 | 8/1991 |
| JP | 04172252 | 6/1992 |
| JP | 06034642 | 2/1994 |
| JP | 2000046842 | 2/2000 |
| JP | 2001-099841 | 4/2001 |
| WO | 98/21595 | 5/1998 |
| WO | 98/57739 | 12/1998 |

* cited by examiner

ASSAY TESTING DIAGNOSTIC ANALYZER

CROSS-REFERENCE TO RELATED APPLICATIONS

This is a continuation-in-part of U.S. patent application Ser. No. 09/840,960 filed Apr. 24, 2001, now U.S. Pat. No. 6,588,625 the content of which is expressly incorporated herein by reference thereto.

FIELD OF THE INVENTION

The present invention relates to a sample and reagent handling system for automatically testing samples with a diagnostic module. More particularly, the invention relates to a sample handling system in which sample and reagent carriers are placed in a loading bay and transported by a transporter to a different location depending on the contents of the carriers. The invention also relates to a diagnostic module with a mechanism for locating the carriers in an aspiration position.

BACKGROUND OF THE INVENTION

In the past, sample handling systems had a single path carrier that would stop at specified locations as desired for testing. In these single path systems, if retesting or preemptive prioritization of a sample were required, the tube would have to travel around the entire module system to be tested or retested. This resulted in either significant delay in testing and retesting or very complex, expensive carrier routing mechanisms.

An example of a single path sample handling device is disclosed in U.S. Pat. No. 5,876,670 to Mitsumaki. In Mitsumaki, a sample carrier, holding a plurality of test tubes, is transferred to the analyzer modules by a transporting belt driven by a motor. All the sample carriers on the transporting belt pass through the sampling position for the first analyzer module and preferably must be transferred to a receiving position to reach the sampling position for the second analyzer module. When a sample needs to be retested, then the operator returns the sample carrier to the beginning of the transporting belt. An urgent sample supply portion is provided on one end of the belt near the sample supply portion, allowing urgent sample racks to be processed before the general racks. In Mitsumaki, the sample handling system processes samples sequentially along the transporting belt and does not automatically retest samples.

Another example of a prior sample handling system is disclosed in U.S. Pat. No. 5,665,309 to Champseix et al. The Champseix et al. device comprises a holding rack for a plurality of test tubes; a sampling station for sampling the contents of a tube; and a gripping device for withdrawing a tube from a selected position on the rack, bringing the tube to the sampling station and returning the tube back to its selected position. The gripping device moves the individual tubes from a rack to the sampling station. However, the Champseix et al., sample handling device does not disclose a method for automatically retesting samples or processing stat samples.

U.S. Pat. No. 5,260,872 to Copeland discloses an automated testing system for the quality testing of production samples, comprising a loading station for receiving a test tube rack containing a plurality of test tubes; a pipetting station; a bead-drop station; and a robotic device having an arm adapted to pick up a test tube rack from the loading station, move the rack to the pipetting station so the fluids can be pipetted into the test tubes; move the rack to the bead-drop station; and return the rack to the loading station in accordance with a computer program. When the Copeland test tube rack is returned to the loading station the tubes may be removed and disposed of and the rack is then loaded with a fresh set of test tubes. The Copeland system does not accommodate for automatic retesting or testing of stat samples.

In the past, reagents have been loaded manually in an automated testing system with a diagnostic module. Reagent replacement is often required in the middle of testing due to consumption of the reagent in a kit or expiration of a reagent. In addition, a reagent may be needed when the system needs to run more test types, analytes, in a day than there are reagent positions in the analyzer. The manual loading of the reagents often resulted in interruption of testing in process or at least a loss of throughput.

SUMMARY OF THE INVENTION

The present invention relates to an assay testing diagnostic analyzer and a handling system thereof. In a preferred embodiment, the handling system includes a loading bay for receiving and holding a plurality of carriers. An identification device is configured for identifying an identifying feature of the carriers or containers to determine the type of contents loaded on each carrier. A transporter is configured for transporting the carriers from the loading bay to a first or second location depending on the determined type of contents on each carrier. A diagnostic process is performed using the contents. The transporter preferably has random access to the plurality of carriers in the loading bay.

In this embodiment, the identification device is configured for identifying the contents of the carriers at least as either samples or reagents. The identification device is associated with the transporter such that the transporter can transport the samples to the first location and the reagents to the second location. Although the loading bay can have a sample loading area and a separate reagent loading area, in a more preferred embodiment, however, a single loading area is provided in which the sample in reagent carriers can be positioned in any order. The identification device is preferably configured for identifying the type of contents independently of where in the loading bay the carriers are loaded. Most preferably, the transporter can transport the carriers from and/or to substantially any location in the loading bay and/or the respective first or second location.

An advantage of the present handling system is that reagents can be loaded and unloaded as regents are consumed or expired, without interrupting the operation of the automated testing or reducing the thoughput of the system. Further, the present handling system includes the ability to exchange one analyte for another,as testing requires, without interrupting the operation of the testing or reducing the throughput of the system.

A first carrier support member of the preferred embodiment, for example an aspiration platform, includes the first location and is disposed for access by a diagnostic module configured for performing the diagnostic process. The transporters can be configured for transporting the carriers from a loading bay to the first carrier support member and additionally to move the carriers between different locations on the first carrier support member. The transporter can preferably move the carriers to and from a plurality of first locations on the carrier support, for example, to position more than one carrier on the support member at any time. In an alternative embodiment, the first carrier support member can include a positioner that can be configured to receive and move the carriers for access by the diagnostic module for testing the contents of at least one of the plurality of the the containers of the carrier.

Preferably, the identifying feature comprises an optically readable feature. The identification device can thus include an optical reader that is capable of reading this feature. The identifying features on the carriers preferably identify them as holding reagents or samples. Preferably, the individual samples and reagents can also be individually identified by the identification device. Alternatively, the carriers can be distinguished by other physical differences that can be detected by a sensor, or the different types of carriers can be in slightly different orientations to allow them to be identified by the position of the carrier. In another embodiment, the identifying feature is an identifiable physical characteristic, such as the height of the carrier.

A programmable controlling computer can control the movement of the transporter and other moving parts of the device based on input data and a pre-programmed priority order for processing the contents on the carriers. In a preferred embodiment, samples to be tested are loaded into the diagnostic system, and reagent carriers that hold containers with reagents are also loaded into the system. The reagent carriers are transported to reagent support members, such as on a carousel, automatically by a transporter. The samples are tested with the appropriate reagents depending on the test being conducted.

A preferred embodiment of a carrier includes at least one container holding portion that is configured for holding a container with a fluid substance, such as the samples or reagents. Preferably the carrier is configured to carry reagents, and may include a stirring member for moving at least one of the holding members with respect to the body of the carrier. The stirring member can include a first engagement portion that is engageable with a second engagement portion of the diagnostic analyzer for moving the container held by the holding portion with respect to the body of a carrier. This movement is preferably in response to relative motion between the carrier body and the second engagement portion. A plurality of holding portions can be provided on the carrier, and preferably fewer than all the holding portions are associated with the first engagement portion such that less than all of the containers are moved with respect to the body. This movement preferably provides for mixing or stirring the contents of the container. In a preferred embodiment, the first engagement member is configured for rotating the container that is associated therewith. The engagement member can be rotatable and configured to roll against the second engagement member. In one embodiment, the first engagement member includes a gear that is configured for meshing with teeth of the second engagement member, or a friction wheel that is in frictional engagement with the second member. In an embodiment in which the carriers are mounted on a carousel, the second engagement member can include a ring gear or friction wheel disposed adjacent a moveable portion of the carousel to mesh with the gear of or contact the friction wheel on the carrier. Thus, as the carousel rotates around the ring gear or friction wheel, the carrier gear or friction wheel causes a rotation of the container mounted therewith. The ratio between the ring gear and the carrier gear can be made at an integer to facilitate the reading of a bar code located on the reagent bottle when the reagent carriers are removed from the reagent carousel.

The preferred holding portions are configured for gripping the containers positioned thereon. Also, the body can have a handle portion to facilitate grasping the loaded carrier by hand. A transporter coupling portion can be provided as well for coupling with the transporter to enable the transporting of the carrier between different locations in the device.

In the preferred embodiment, a positioning device is configured for receiving and positioning the carriers for access by the diagnostic module. This positioning device is preferably provided for receiving the reagent carriers and includes the second location and is the second carrier support member. A retention member associated with the positioning device is configured for locking the carrier to the positioning device. The retention member is preferably operably associated with the transporter for releasing and including the carrier for the transporter to transport the carrier therefrom. This operative association can be provided by a mechanical connection activated by contact therebetween, an electrical connection, or it can be provided by the controlling computer, which tracks the positions of the transporter and the positioning device.

The preferred positioning device is a rotatably driven carousel that is driven to provide access to the contents of the carrier by the diagnostic module. An activation member of the preferred embodiment is operably associated with the transporter for releasing the carrier upon contact between the transporter and the activation member. A carrier-locking member is preferably configured for moving with respect to the carousel in association with the carrier to lock and unlock the carrier. The activation member is preferably displaced by the transporter to move the carrier-locking member to cause the locking and/or unlocking of the carrier. Preferably, the locking member displaces the carrier with respect to the carousel to move the carrier into a locked position. The carousel is preferably rotatable or otherwise movable with respect to the activation member, and the locking member is preferably mounted to the carousel. The activation and the locking member are disposed such that the activation member in the inactive position does not interfere with the locking member during the carousel rotation.

The retention member also preferably comprises a latching member configured for latching to a latchable portion of the carrier in the locked position, preferably upon relative movement between the latching member and the latchable portion. The locking member is preferably moveable with respect to the carousel and is associated with the carrier to move at least a portion of the carrier with respect to the latching member for locking and unlocking the carrier. Additionally, the locking member can have a tab that is received in the recess of the carrier to slide the carrier with respect to the latching member.

A carrier sensor can be provided for detecting the presence of the carrier on the positioning device. This carrier sensor can be, for example, a Hall effect, optical or a capacitive sensor.

Additional advantages of the invention will be realized and attained by the apparatus and method particularly pointed out in the written description and claims hereof, as well as from the appended drawings. It is to be understood that both the foregoing general description and the following detailed description are exemplary and are intended to provide further explanation of the invention claimed.

DETAILED DESCRIPTION OF THE PREFERRED EMBODIMENTS

Figure 1:
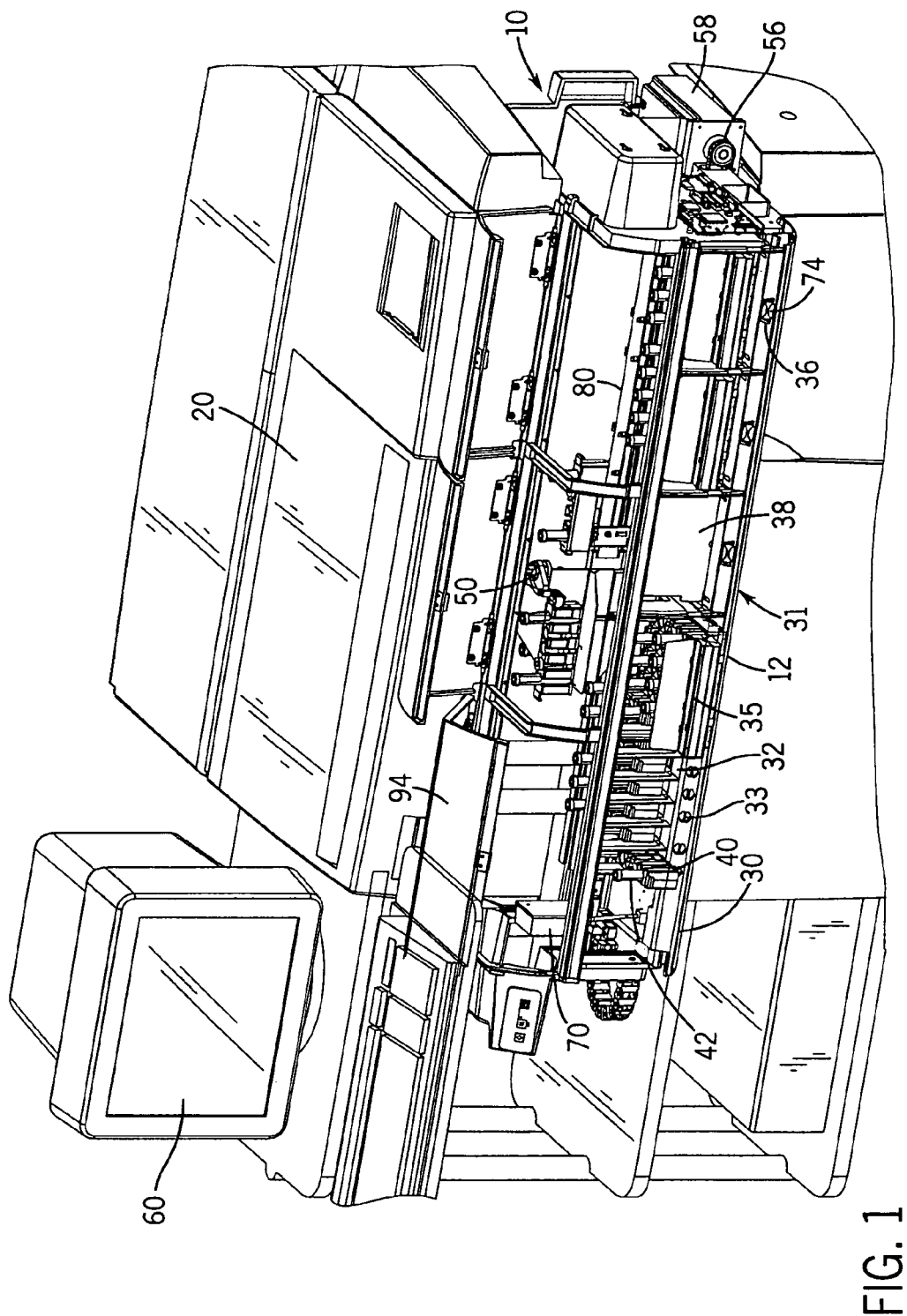
FIG. 1 is a perspective view of a preferred embodiment of the sample handling system of the present invention.

The present invention relates to a random sample and reagent handling system for moving samples and reagents to and from a diagnostic module for automatic testing and retesting. The random handling system includes a loading rack for receiving a plurality of carriers. The carriers can include several tubes filled with samples. In a preferred embodiment, the sample carriers are arranged in a stationary linear array on a loading rack positioned in front of the diagnostic modules. The operator may load the carriers individually or in trays for convenient handling of multiple carriers. Individual carrier slots are provided for loading high priority or stat samples that require immediate processing.

A robotic device is provided to transport the carriers to and from the loading rack and to and from a carrier positioner adjacent the diagnostic module(s). The robotic device has an arm, which is controlled by a programmable computer, moving the carriers as required for testing and retesting. The system includes software that allows users to flexibly configure rules or criteria for retesting samples. These rules can also be utilized to change to another type of test depending on the results of a previous test. This can be a very cost effective approach that when utilized minimizes operator involvement in real time. The system also includes a software capability that can suspend the operation of the sampler handler in the event the user decides to change the test request(s) for a particular sample after loading the carrier.

The carrier positioner is located adjacent a diagnostic module for positioning the carriers so the samples selected for testing can be aspirated by a probe. The positioner includes a carriage connected to a lead screw driven by a stepping motor in response to commands from the programmable computer. In a preferred embodiment, the carrier positioner can accommodate at least two carriers, allowing the processing module to test one carrier while the transporter loads another carrier onto the positioner to maintain the system throughput.

A barcode reader is provided to read carrier and container identification. A bar code reader in the system reads bar coded labels attached to the carriers and the sample tubes or reagent bottles as the robotic device passes the carriers by the reader.

Only one robotic device and barcode reader are preferably used for the present system, regardless of size. The invention can be dynamically configured for variable queue sizing depending on the user's particular workload. Additionally, the total capacity of the system can be changed based on peak loading requirements that vary across testing segments in the laboratory.

In operation, the robotic arm picks up a carrier from the loading rack and travels past the bar code reader to identify the carrier and samples. Tests previously programmed in the computer are assigned to each tube in the carrier. The robotic arm delivers the carrier to be tested to the carrier positioner. The positioner is controlled by the computer to move the carrier to a predetermined location adjacent a pipetter on the diagnostic module. The pipetter aspirates samples from the tube for testing. When the tests are completed on all the tubes in the carrier, the robotic arm loads the carrier and returns the carrier to its designated location in the loading rack. While the tubes of one carrier are being aspirated, a second carrier can be moved to the carriage.

The carrier handling system can include more than one diagnostic module. For example in one preferred embodiment, the carrier handling system includes two diagnostic modules, a clinical chemistry test module and an immunoassay module. A carrier positioner is provided for each diagnostic module in the system.

The present invention provides a modular random sampling system that can be adapted to a variety of diagnostic modules. The present carrier handling system is modular and scalable to different sizes of processing modules and may be used for single or multiple module systems. The system provides random access to carriers on the loading rack. This random access capability allows the system to access and process high priority samples rapidly. This capability also allows the system to balance the workload of multiple processing modules with different throughput capabilities. After samples are processed initially, the sample carriers are returned to their slots in the loading area and then accessed again when the initial testing is complete to provide automated retest capability. This automated retest capability does not require any additional intervention by the operator. Random access assures the samples to be retested can be processed in the shortest possible time. The system is mechanically simple, which minimizes system cost and maximizes system reliability. The present system is self-contained and can be assembled and tested independently of the processing modules for ease of manufacture and installation in the field.

A system is also provided that processes samples for testing and retesting in a faster time and with more reliability than previous handling systems. The sample handling system of the invention can additionally provide faster processing of high priority samples while maintaining throughput of routine test samples.

A system can be provided having a robotic assembly for moving a carrier with a plurality of test samples from a loading rack to a sample testing area and returning the carrier to the loading rack and having a programmable computer for (1) controlling the robotic assembly, (2) selecting carriers for testing based on predetermined priority, (3) achieving positive identification of the carriers and samples, and (4) identifying a breach of positive identification when an access door has been opened or a carrier has been removed prematurely.

Figure 2:
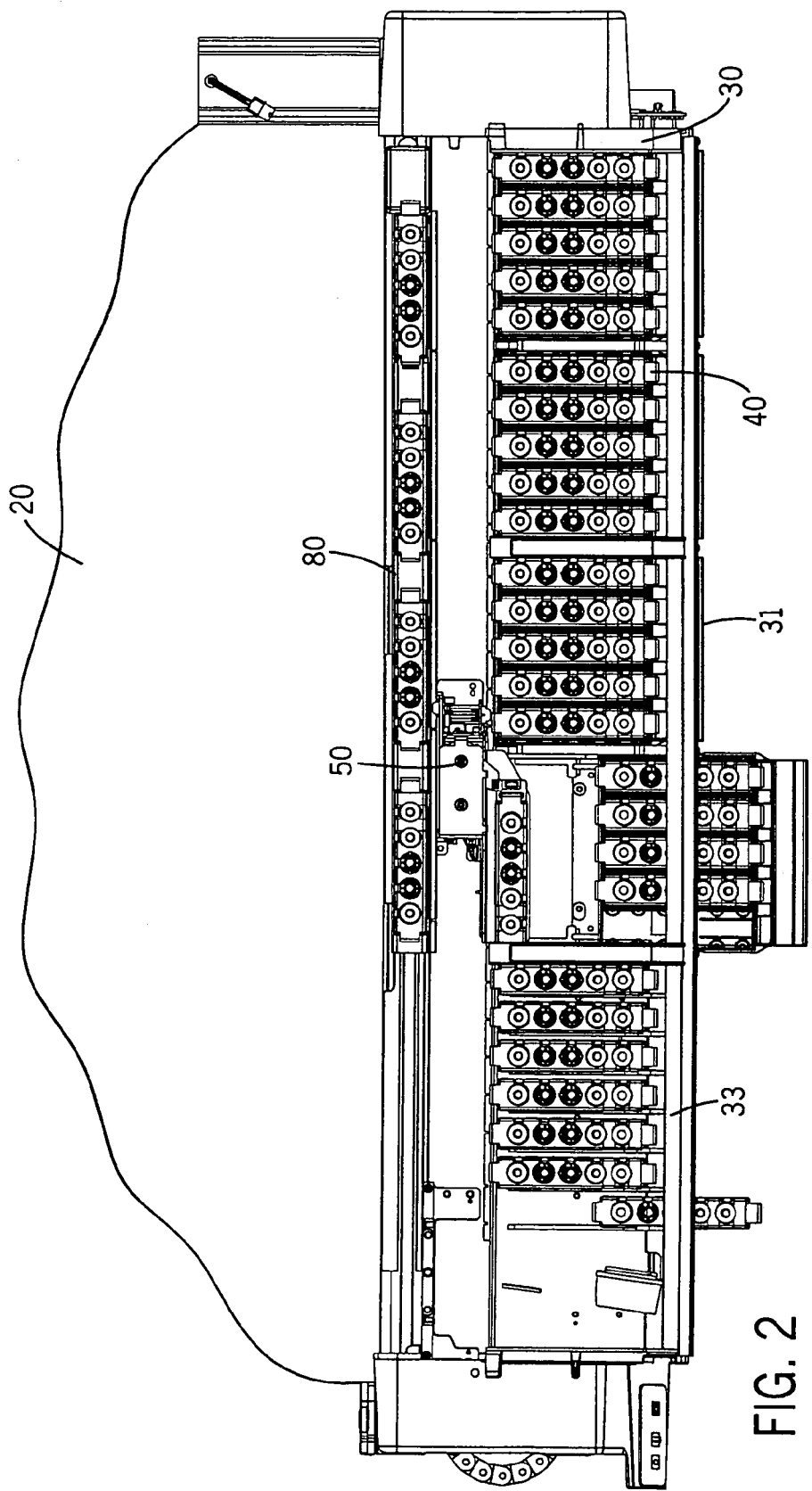
FIG. 2 is a top plan view of the sample handling system of FIG. 1 with access doors removed.

A preferred embodiment of the invention is a carrier handling system, generally designated by the numeral 10. As shown in FIGS. 1 and 2, the present handling system 10 includes a loading rack 30 with a plurality of slots 32 for receiving a plurality of carriers 40. Each carrier 40 can hold a plurality of containers 42, such as tubes or cups, filled with samples. In this example, each carrier 40 can hold five tubes 42. However, the carriers 40 can be configured to hold either more or less tubes 42 depending on the system requirements.

The sample carriers 40 are arranged on the loading rack 30 in a stationary linear array near the processing modules 20. The operator can load the carriers 40 onto the loading rack or platform 30 of a loading bay individually into slots 32 or in trays 35 for convenient handling of multiple carriers. The loading rack 30 can be configured in different shapes such as circular with slots aligned around the circular tray. The loading rack 30 includes a routine loading area 31 and an urgent or stat sample area 33. In a preferred embodiment of the present invention, the routine loading area 31 comprises a plurality of bays 36, each bay 36 accommodating a tray 35. Each bay 36 includes a door 38 attached to the loading rack 30. Each door 38 includes a latch that is automatically released by insertion of a tray 35. This latch is preferably difficult to actuate by hand to prevent an operator from affecting the operation of the carriers 40.

The carriers 40 may be loaded onto a tray 35 before loading the tray 35 into the loading rack 30 from the front 12 of the handling system 10. Alternatively, a carrier can be loaded onto the tray previously loaded onto the loading rack 30. In this example, a tray 35 accommodates up to five carriers and the loading rack accommodates seven stat carriers 40 and four routine trays 35 holding up to 25 samples each. However, the loading rack 30 may be configured differently to accommodate peak loading requirements that vary across testing segments in the laboratory.

The carriers 40 are positioned in the tray slots until selected for testing or retesting. A carrier 40 is released for unloading immediately after retest or after all tests in the carrier 40 are complete and no retests are required. A tray 35 is released for unloading when all the carriers 40 in the tray 35 are released for unloading. A high priority or stat carrier 40 is loaded into the high priority sample area 33. A carrier 40 located in the high priority area 33 is transferred to the carrier positioner 80 for aspiration and then is returned to the stat area 33 until a programmable computer 60 determines if a retest is needed. A stat carrier 40 is released for unloading after all tests are completed and any retest requests are aspirated.

A plurality of status indicators 74 are provided to indicate to the operator when a completed tray 35 or an individual carrier 40 in the high priority area 33 may be removed. For example, the status indicator light 74 is green to indicate the corresponding tray 35 or carrier 40 can be accessed or the status indicator light 74 is amber to indicate the tray 35 or carrier 40 is in process and should be left in place until completed.

The present sample handling system 10 includes a means for detecting that a new tray 35 or new carrier 40 in the high priority area has been loaded. A loading rack sensor 98 (not shown) is located in each bay or stat slot to detect the presence of a tray or carrier respectively. If a new tray is detected the contents of the tray 35 are scanned by a first sensor 102 on the carrier transporter 50 to determine if any carriers are in the tray.

Figure 6:
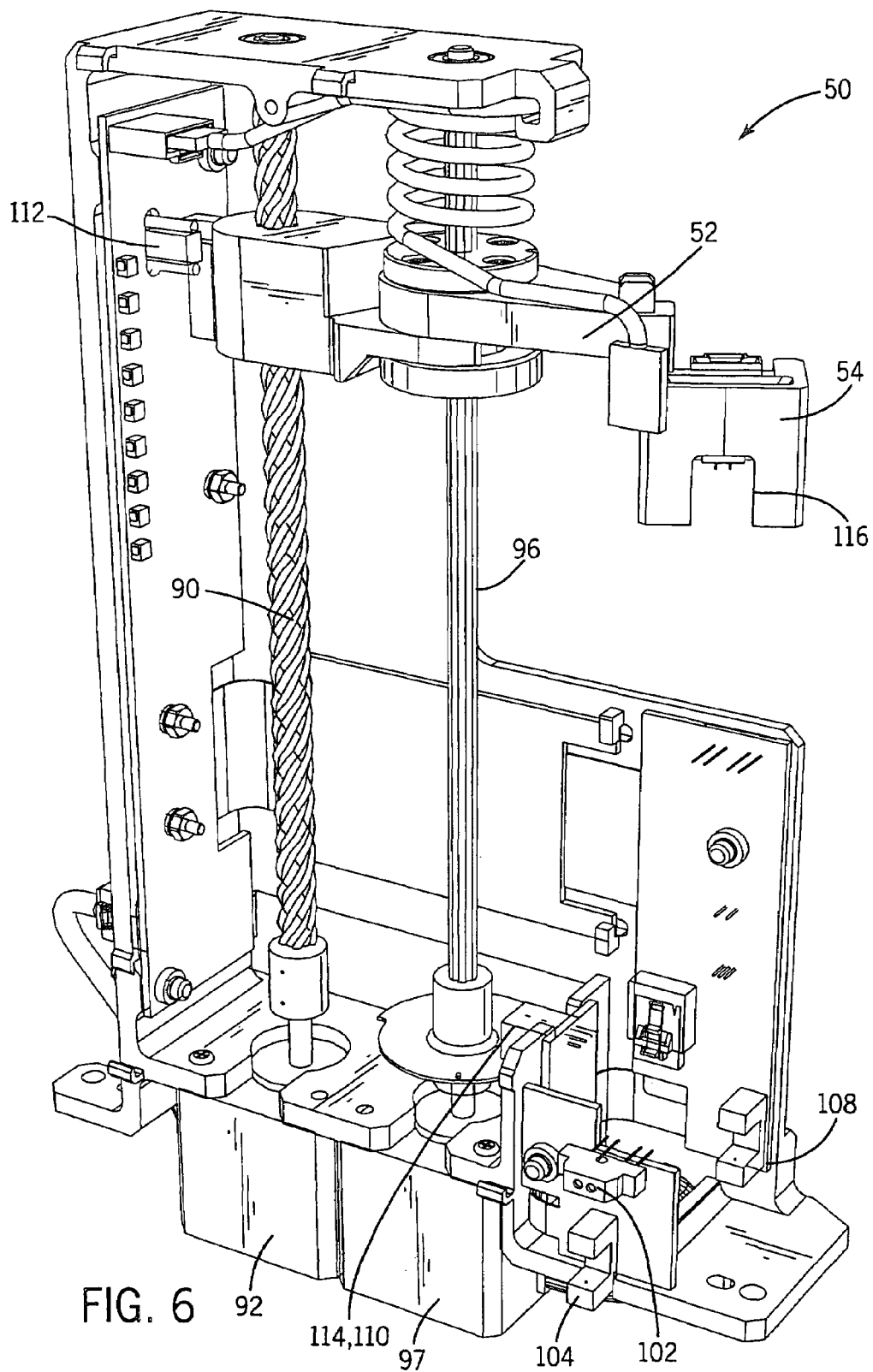
FIG. 6 is a perspective view of a preferred embodiment of a transporter.

In a preferred embodiment, the sample handling system 10 includes a carrier transporter 50 that consists of a robotic device having a robotic arm 52 to move the carriers 40 as required for testing and retesting (see FIG. 6). The robotic arm 52 has a gripper device 54 that picks up the carrier 40 by a support tab 48. The robotic transporter 50 includes a drive motor 58 that is controlled by a programmable computer 60. In the preferred embodiment, the robotic arm 52 traverses the length of the loading platform 30 by a timing belt 56. However, it is understood by a person skilled in this art that other means can be used to move the robotic arm 52.

The transporter 50 is capable of lifting a carrier 40 a height just slightly more than the total height of the carrier 40 holding a tube 42 in the loading rack 30. The vertical motion of the transporter 50 is created by a lead screw 90 driven by a stepping motor 92. The robot transporter 50 can also rotate a carrier 40 through a 210 degree range of motion between positions for barcode reading, access to carrier slots, access to a carrier positioner 80, and access to a reagent storage location. The rotational motion of the transporter 50 is provided by a spline shaft 96 coupled to a stepping motor 97. The spline shaft 96 allows the robotic arm 52 to move vertically while maintaining accurate angular positioning. Although the preferred embodiment includes specific means to move the robotic transporter, it is understood by a person skilled in this art that other means could be used to move the transporter 50.

Figure 5:
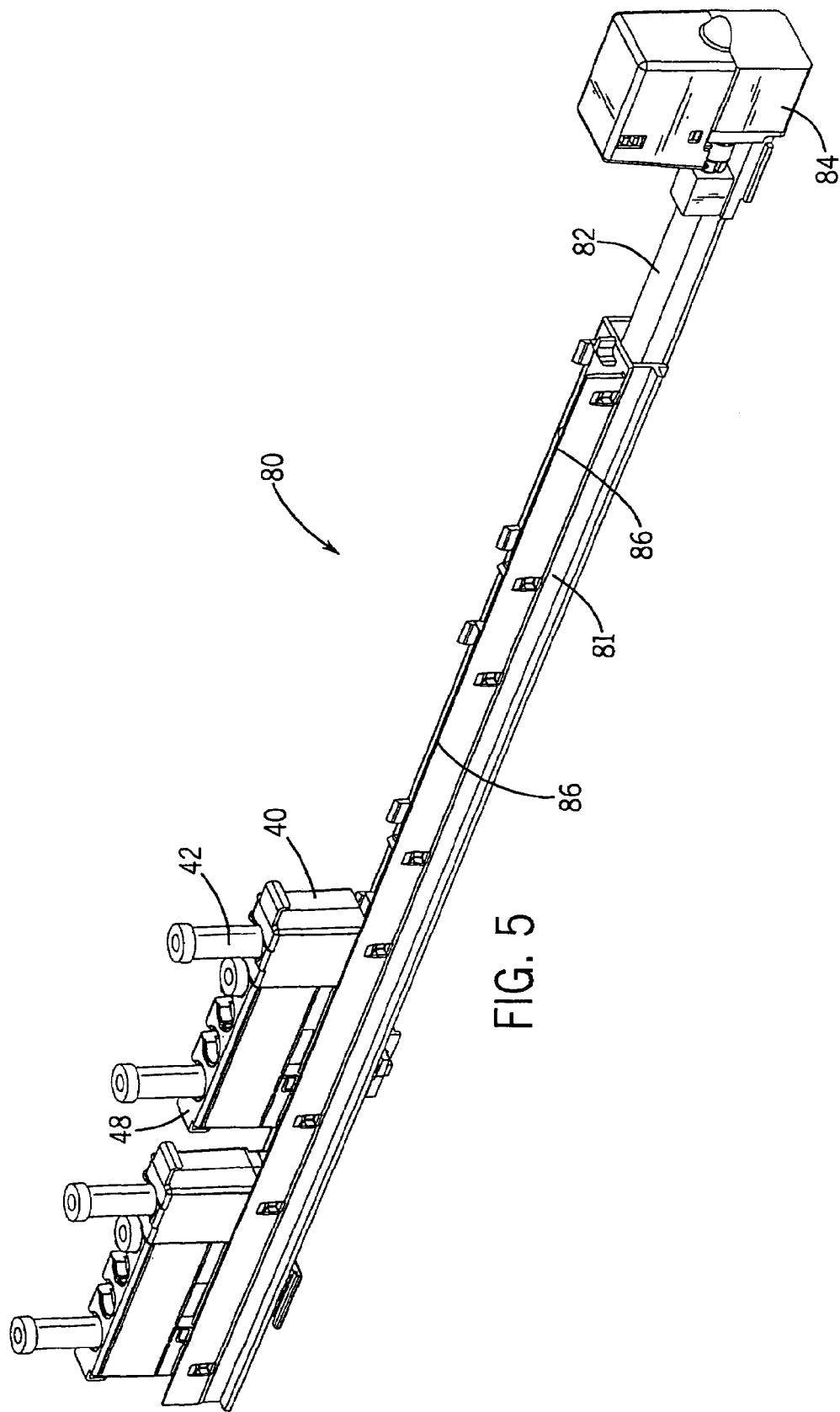
FIG. 5 is a perspective view of a preferred embodiment of a carrier positioner.

The present sample handling system 10 also includes a carrier positioner 80 located adjacent a diagnostic module 20 for conducting tests on the samples in the test tubes 42 (see FIG. 5). In the preferred embodiment, the carrier positioner 80 has a plurality of openings 86 for receiving carriers. The positioner 80 can position at least two complete carriers underneath the testing point(s) of a processing module, allowing the processing module to aspirate from one carrier 40 while the transporter 50 loads another carrier 40 on the positioner 80 to maintain system throughput. The carrier positioner 80 includes a carriage 81 on a lead screw 82 driven by a stepping motor 84 in response to commands of the computer 60. Although in the preferred embodiment the positioner 80 is driven by a lead screw 88, the positioner 80 could be driven by other known driving means such as a belt, a chain, an air cylinder, or a linear motor. The positioner 80 may be a variety of configurations, including having multiple openings 86 for routine carriers and high priority carriers.

In a preferred embodiment, the carrier positioner 80 has four openings 86 to accommodate the needs of several different types of processing modules using common hardware to reduce the overall product cost of the system (see FIG. 5). The positioner 80 is configured to adapt to a variety of diagnostic modules 20. For example, two openings may be used for one pipetter and the other two openings for a different pipetter in the same diagnostic module 20. Alternatively, two openings may accommodate solely high priority sample carriers while the other two openings accommodate routine sample carriers.

The robot transporter 50 executes the following six basic carrier handling operations: 1) pick up carrier 40 from loading rack 30; 2) place carrier 40 into loading rack 30; 3) place carrier 40 onto positioner 80; 4) pick up carrier 40 from positioner 80; 5) present carrier 40 to a barcode reader 70; and 6) scan trays 35 for carriers 40.

In a preferred embodiment of the present invention, the robot transporter 50 includes nine sensors for monitoring the correct operation of the system. Due to the unique value and hazards of the biological samples being transported, a high degree of capability to monitor and verify the operation of the transporter 50 is important. A first reflective sensor 102 on the transporter 50 is used to determine the presence of a carrier 40 in a tray 35 or slot 32. A second (carrier slot alignment) sensor 104 is used to verify correct alignment between the transporter 50 and the carrier slots on the loading rack for pick up and placement of the carriers. A third (carrier positioner alignment) sensor 106 is used to verify alignment between the transporter and the openings 86 in the positioner 80. A fourth reflective sensor 107 is used to determine if a carrier 40 is present on the positioner 80. The horizontal, rotational, and vertical motions of the transporter 50 are monitored by fifth, sixth, and seventh sensors 108,110,112. An eighth sensor 114, positioned with the rotational motion sensor 110, is used to verify the correct rotational position of the robotic arm 52. Located on the robotic arm 52 is a ninth sensor 116 used to verify that the carrier 40 is properly engaged in the arm 52 for safe transport. Although the preferred embodiment includes the above-described nine sensors, it is understood by a person skilled in this art that other means could be used to monitor and verify the operation of the transporter 50 and the robotic arm 52.

A bar code reader 70 is included in the present sample handling system to read carrier and sample identification. Bar coded labels are attached to the carriers 40 and, optionally on the sample tubes 42. The carrier 40 is scanned once with a barcode reader 70 when the carrier 40 is first selected. After being scanned, the carrier 40 is moved by only the transporter 50 or the linear positioner 80. At this point, all motions of the carrier 40 generate position and alignment feedback to the computer 60, so the carrier identification only needs to be read by the barcode reader 70 once.

Many types of diagnostic modules 20 can be employed with the present random sampling handling system 10, including immunoassay modules or clinical chemistry test modules. Examples of suitable diagnostic modules include ARCHITECT.RTM.i1000, i2000, and c8000 processing modules, manufactured by Abbott Laboratories, Abbott Park, Ill.

In a preferred embodiment of the sample handling system 10 a plurality of access covers 94 are positioned over the loading rack 30. When an access door 94 is opened, an interlock connected to the access cover 94 preferably will indicate a breach of positive identification, preferably requiring the barcode reader 70 to rescan the carriers 40.

During operation of the present carrier handling system 10, an operator loads the trays 30 or individual carriers 40 onto the loading rack 30. Either the operator inputs into the computer the patient sample identification and the test orders or this information may be downloaded into the computer 60 from a lab information system. A test order may require a plurality of separate assays. Once a sample is loaded, the programmable computer 60 determines the order of the different sample tests based on a preprogrammed priority. The system detects the presence of the carriers 40 and selects one for sampling. The computer 60 activates the robotic transporter 50 to pick up the selected carrier 40 from the loading rack 30 and transport the carrier 40 past the bar code reader 70 to identify the carrier 40 and the sample tubes 42, the bar code data is sent to the programmable computer 60. Tests previously programmed in the computer 60 are assigned to each tube 42 in the carrier 40. The transporter 50 then delivers the carrier 40 to the positioner 80. Software in the computer 60 controls the movement of the positioner 80, moving the carrier 40 to a predetermined location adjacent a testing site or pipetter on the diagnostic module 20. The pipetter withdraws the sample from a tube 42 for testing.

When the tests are completed on all the tubes 42 in the carrier 40, the robotic arm 52 loads the carrier 40 and then moves and returns the carrier 40 to its assigned location on the loading rack 30. While the tubes 42 of one carrier 40 are being aspirated, a second carrier 40 can be loaded onto the carriage 81 for testing. At this point, the status indicator 74 will show a hold status for the carrier 40 until the computer 60 makes the retest decision. If a retest is needed, the carrier 40 will be selected again with the same process described above, but without a bar code scan. The robot 50 continues to pick up carriers 40, scan and place the carriers 40 as required. The status indicator 74 at each tray 35 or slot 32 will show a completed tray of carriers 35 or carrier 40 when retesting is not required. The operator should remove the completed carrier 40 or tray of carriers 35 when they have been released for unloading.

Positive identification of the carriers preferably is considered violated if an access cover 94 of the sample handling system 10 is opened. When an access door 94 is opened all carriers 40 preferably must be rescanned before further testing to provide positive identification. Further, positive identification of a carrier 40 is violated if a carrier 40 or a tray 35 on the loading rack 30 is removed prematurely. At this point the carrier 40 or tray 35 that was removed prematurely preferably must be replaced and rescanned. Slot and tray sensors 98 are monitored continuously to identify such violation of the positive identification. The programmable computer 60 rapidly checks the status of each individual tray or carrier sensor 98 in sequence. If a change in sensor state is observed, the computer 60 can determine that a carrier 40 or tray 35 has been removed and the identity of the contents can no longer be assured until the carriers 40 in question are re-scanned.

In the preferred embodiment, the robot arm 52 cannot access the linear positioner 80 while it is moving. For example, if the positioner 80 accommodates two carriers 40, and two carriers 40 are already on the positioner 80, no preemption is allowed for a high priority or stat sample. The high priority testing preferably must wait until the carrier 40 in process is complete. At this point, the completed carrier 40 may be unloaded, the stat sample will be loaded and processed immediately. However, if only one carrier 40 is on the positioner 80, the stat or priority carrier may be loaded immediately and after the current sample is completed, the stat or priority carrier will be positioned for aspiration. Aspiration will resume on the remaining routine samples after all the tube samples on the stat carrier are aspirated.

The computer software preferably includes a preprogrammed or programmable priority order for processing samples. For example, the carriers can be selected for processing according to the following priority: 1-unload completed carriers; 2-move aspirated carriers to the loading rack; 3-stat or priority retests; 4-stat or priority tests; 5-stat or priority carrier pick, scan and move to holding area; 6-routine retests; 7-routine tests; 8-routine carrier pick, scan & move to holding area. This ordering of sample priorities has been shown to result in rapid response to high priority samples and maintaining high system throughput. It is understood by one skilled in the art that other priority schemes may be implemented to achieve different levels of performance and responsiveness.

Figure 3:
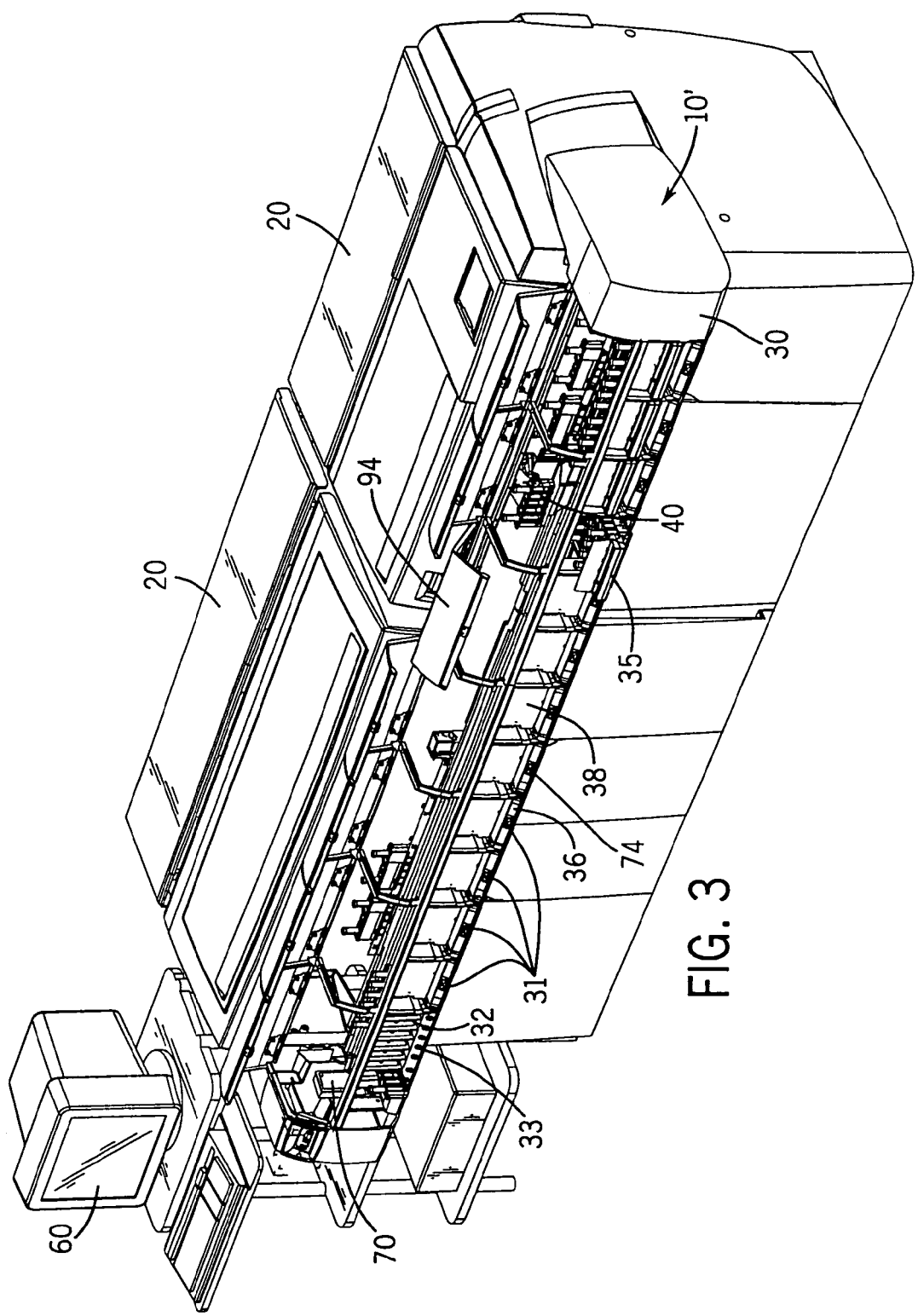
FIG. 3 is a perspective view of a preferred embodiment of the sampling handling system with two diagnostic modules.
Figure 4:
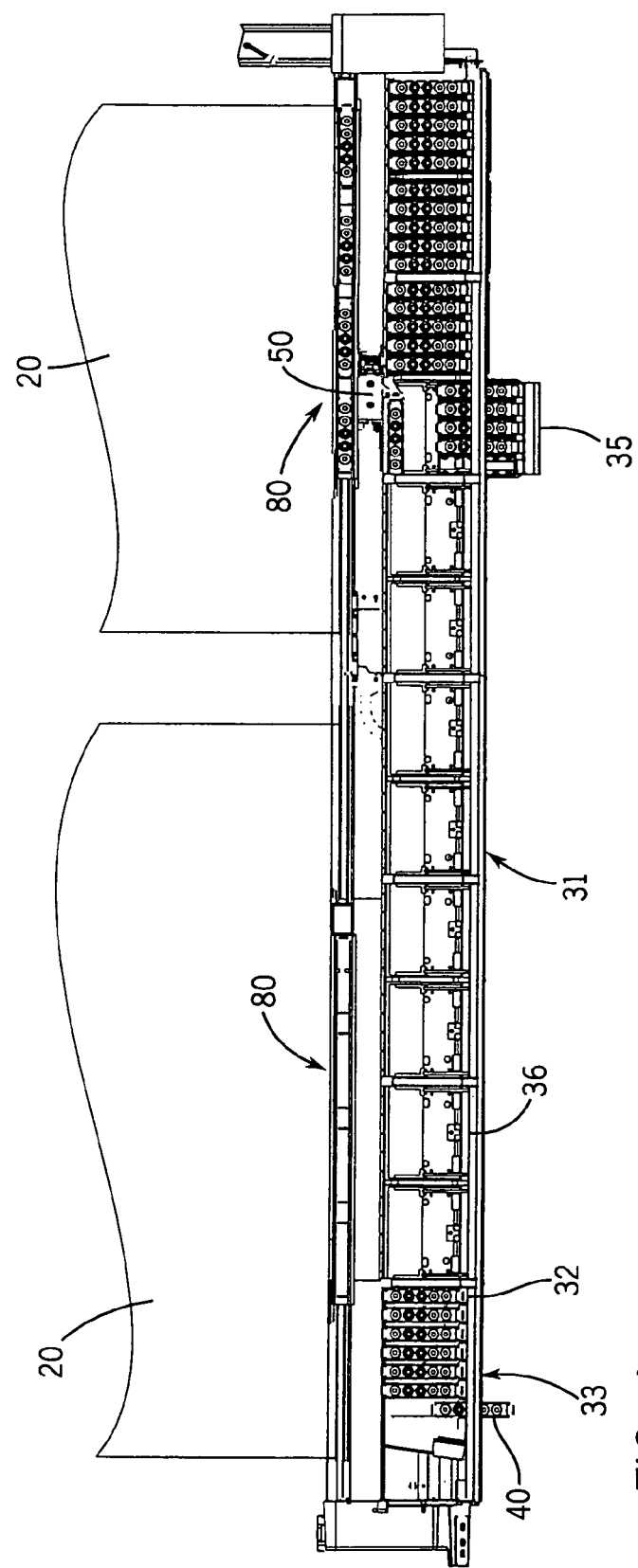
FIG. 4 is a top plan view of the sample handling system of FIG. 3 with access doors removed.

Another preferred embodiment of the carrier handling system is shown in FIGS. 3 and 4 with a plurality of diagnostic modules 20. This alternative embodiment is very similar to that depicted in FIGS. 1 and 2. Accordingly, like numerals in FIGS. 3 and 4 indicate the same elements as defined in connection with FIGS. 1 and 2.

The carrier handling system 10' in FIGS. 3 and 4 includes at least two diagnostic modules. The diagnostic modules 20 could include immunoassay, clinical chemistry, hematology, or other known diagnostic modules, or a combination of these modules. A carrier positioner 80 is provided for each diagnostic module 20. A sample handling system 10' with a plurality of diagnostic modules 20 enhances the productivity in a lab. Further a multiple module system reduces the requirement to separate or aliquot samples for distribution to different systems. In the present system, samples can be tested with the different modules without removing them from the system. This multiple module system also reduces the space requirements in a lab and can lower the costs of operation.

As shown in FIG. 3, a preferred embodiment of the carrier handler system 10' includes a loading rack 30 having seven urgent or priority carrier slots 32 and 12 bays 36 for receiving routine trays 35 holding five carriers 40 each.

Only one carrier transporter 50 and barcode reader 70 are preferably used for the present system, regardless of size. Appropriate control software is used for the present system to select carriers 40 for testing and retesting based on a predetermined priority, direct the operation of the mechanisms, and monitor the system for correct operation.

The present sample handling system is modular and scalable to different sizes of processing modules and may be used for single and dual module systems. The system provides random access to sample carriers in the loading platform. This random access capability allows the system to access and process high priority samples rapidly. This capability also allows the system to balance the workload of two processing modules with different throughput capabilities. After samples are processed initially, the samples can be returned to the loading platform and then accessed again when the initial testing is complete to provide automated retest capability. This automated retest capability preferably does not require any additional intervention by the operator. Random access assures the samples to be retested can be processed in the shortest possible time. The system is mechanically simple, which minimizes system cost and maximizes system reliability. The present system is self-contained and can be assembled and tested independently of the processing modules for ease of manufacture and installation in the field.

Several features are included in the present sample handling system to prevent incorrect carrier placement. First, the second and third sensors 104 and 106 on the transporter 50 verify correct alignment of the carrier 40 with the linear positioner 80 and the loading rack 30 respectively. In addition, the first sensor 102 verifies the presence of a carrier 40 on the loading rack 30 and the fourth sensor 107 (not shown) verifies the presence of a carrier 40 on the positioner 80. Further, the system includes frequent software verification of the operation of the sensors.

Figure 7:
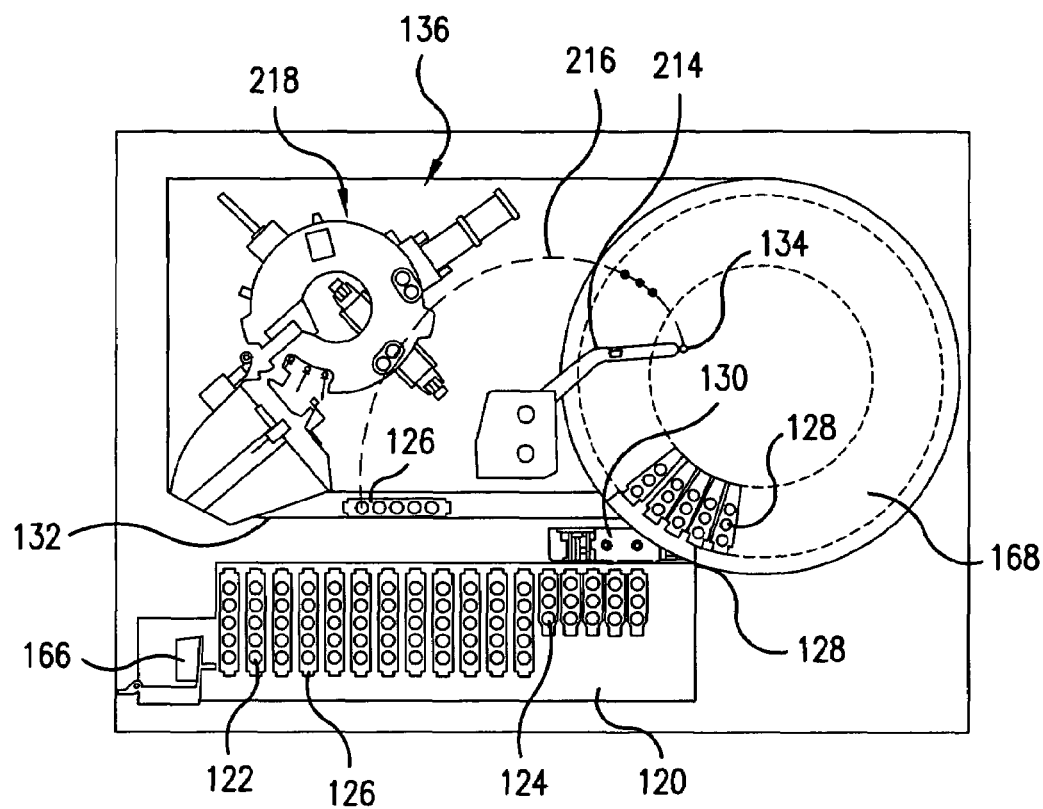
FIG. 7 is a top view of another embodiment of a diagnostic analyzer system according to the present invention.

Referring to FIG. 7, another embodiment of a diagnostic analyzer system includes a loading bay 120 with a loading tray, which is configured to receive both sample and reagent containers 122,124. To insure stability of samples and reagents refrigeration may be included in the loading tray area. Preferably, the sample and reagent containers 122,124 are held in sample and reagent carriers 126,128, respectively. Robotic transporter 130 is configured for linking to and transporting both the sample and reagent carriers 126,128. The robot transporter 50 can rotate a carrier 40 through a 210 degree range of motion between positions for barcode reading, access to carrier slots, access to a carrier positioner 80, and access to the reagent storage location. The transporter 130 preferably has random access to any of the sample carriers 126 or reagent carriers 128, regardless of where they are positioned in the loading bay 120. In FIG. 7, the reagent carriers 128 are shown in groups to the right of the sample carriers 126, but the preferred transporter 130 and loading bay 120 can accommodate the carriers 126,128 in any position and in any order, even with reagent carriers 128 interspersed between sample carriers 120. In an alternative embodiment, however, separate bays are provided for sample carriers 126 and reagent carriers 128.

Figure 8:
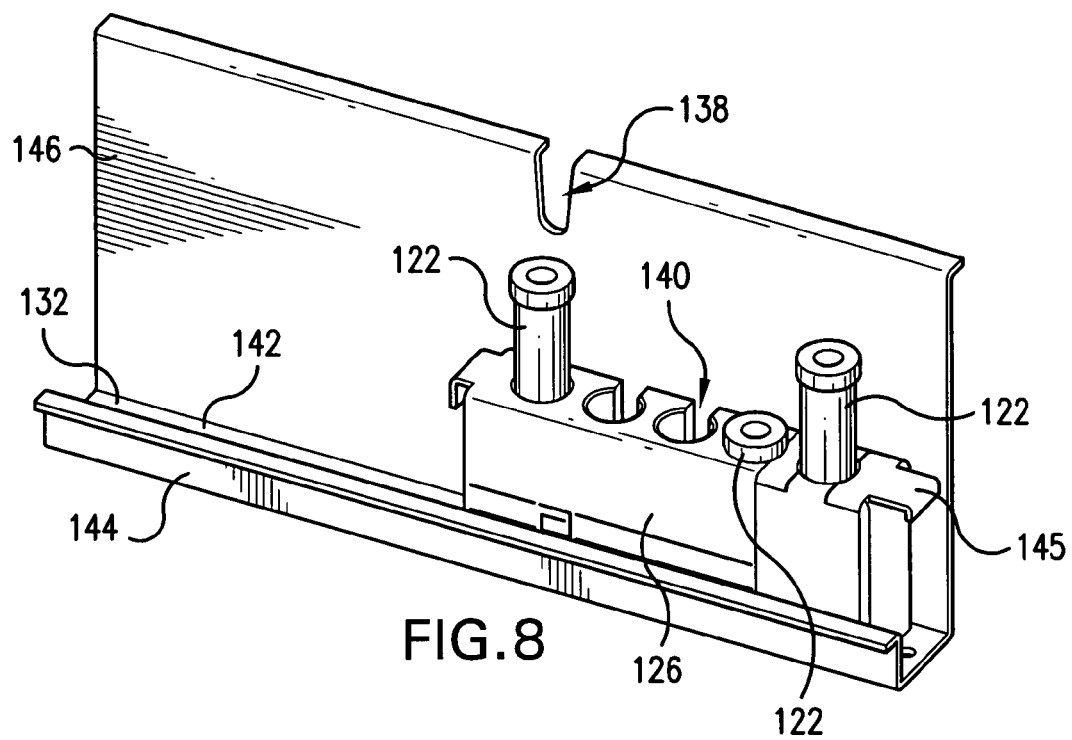
FIG. 8 is a perspective view of an aspiration platform thereof, including a sample receiving tray.

The preferred embodiment preferably has an aspiration tray with a sample positioning shelf 132, as shown in FIG. 8, which can be free of any mechanism to move the sample carrier therealong. The transporter 130 is preferably configured to reposition the sample carriers 126 along the shelf 132 as needed for access by the diagnostic module 136. The sample container 122 that is to be accessed by the pipetter 134 of the diagnostic module 136 is positioned in a pipetting location, which is preferably adjacent a notch 138 in an upright wall of the shelf 132. The notch 138 is configured to receive the end of the pipetter 134 as it is moved downwardly towards the contents of the sample container 122. For access to other sample containers 122 and the sample carrier 126, the transporter 130 repositions the sample carriers 120 along the shelf 132. The shelf 132 is preferably sufficiently large to accommodate a plurality of sample carriers 126, each of which can be repositioned by the transporter as needed for access by the pipetter 134. Shelf 132 preferably has a bottom support surface 142 and a front upright wall 144 that is sufficiently high to prevent the sample carrier 126 from sliding off the shelf, as well as an upright back wall 146. The back wall 146 is preferably taller than the front wall 144, the carrier 126, and any containers 122 that are held in the carrier 126, and promotes sterility in the diagnostic module 136, which is preferably disposed behind the back wall 146.

In the preferred embodiment, the sample carrier 126 has slots 140 aligned axially with respect to the openings in which the sample containers 122 are carried. The slots 140 permit scanning of a bar code or other identifying feature that is present on the containers 122. In an alternative embodiment, another bar code or other identifying feature can also or alternatively be present on the sample carrier 126 itself.

Figure 9:
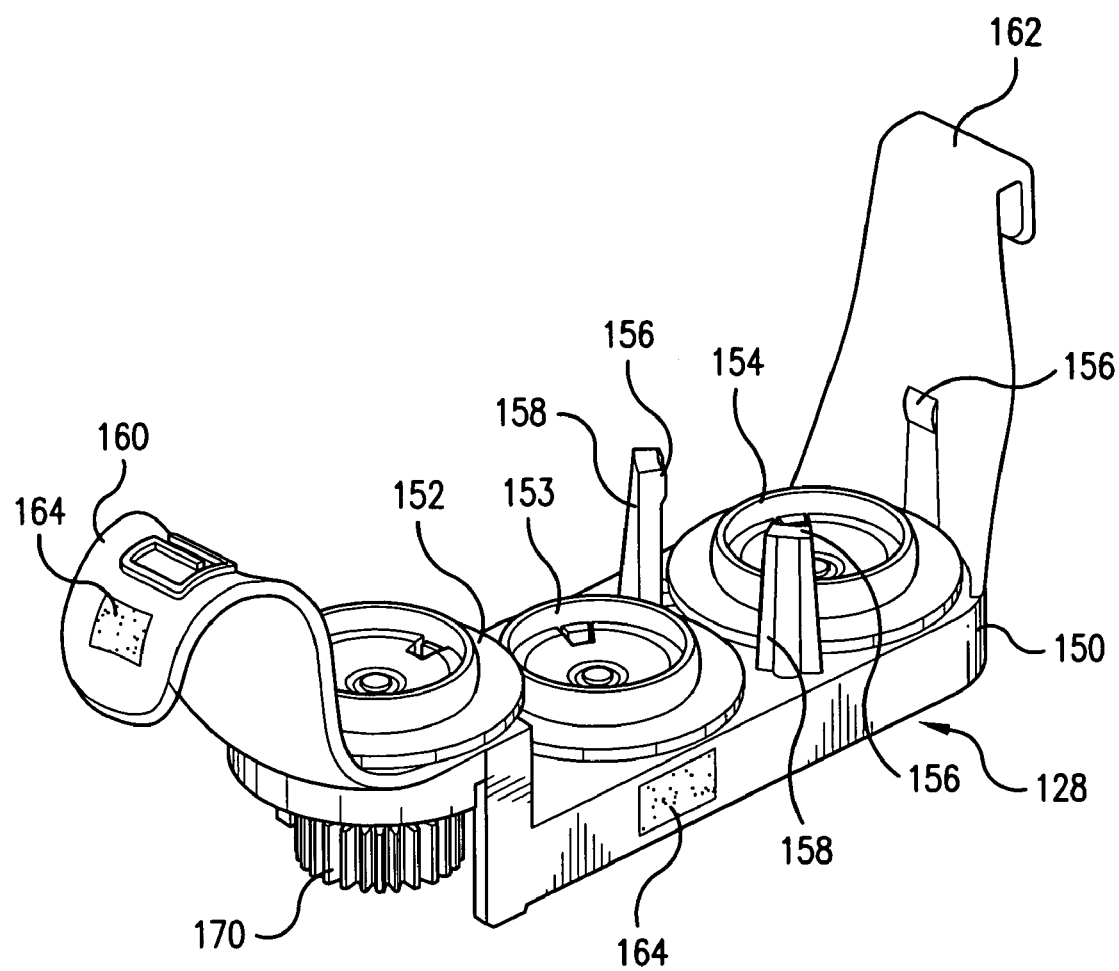
FIG. 9 is a perspective view of a preferred embodiment of a reagent carrier.

A preferred embodiment of a reagent carrier 128 is shown in FIG. 9. The carrier 128 has a carrier body 150 that includes holding portions 152–154, each of which is configured for holding a reagent container 124. The three holding portions 152–154 preferably have a structure for a snap-fit connection to the base of a container 124. Holding portion 154 additionally includes nubs 156, which can be supported on upstanding posts 158 and which are configured to clip about an enlarged diameter portion of the base of an alternative reagent container (not shown) that does not have the snap-fit features located on other reagent containers.

Holding portion 152 is configured for moving with respect to the carrier body 150 to move a reagent container 124 that is attached thereto for a constant mixing or stirring effect. This is desirable, for example, when the reagent includes microparticles that require constant motion to maintain a generally homogenous suspension. This holding portion 152 is movable with respect to the body 150 to produce this relative motion.

Figure 10:
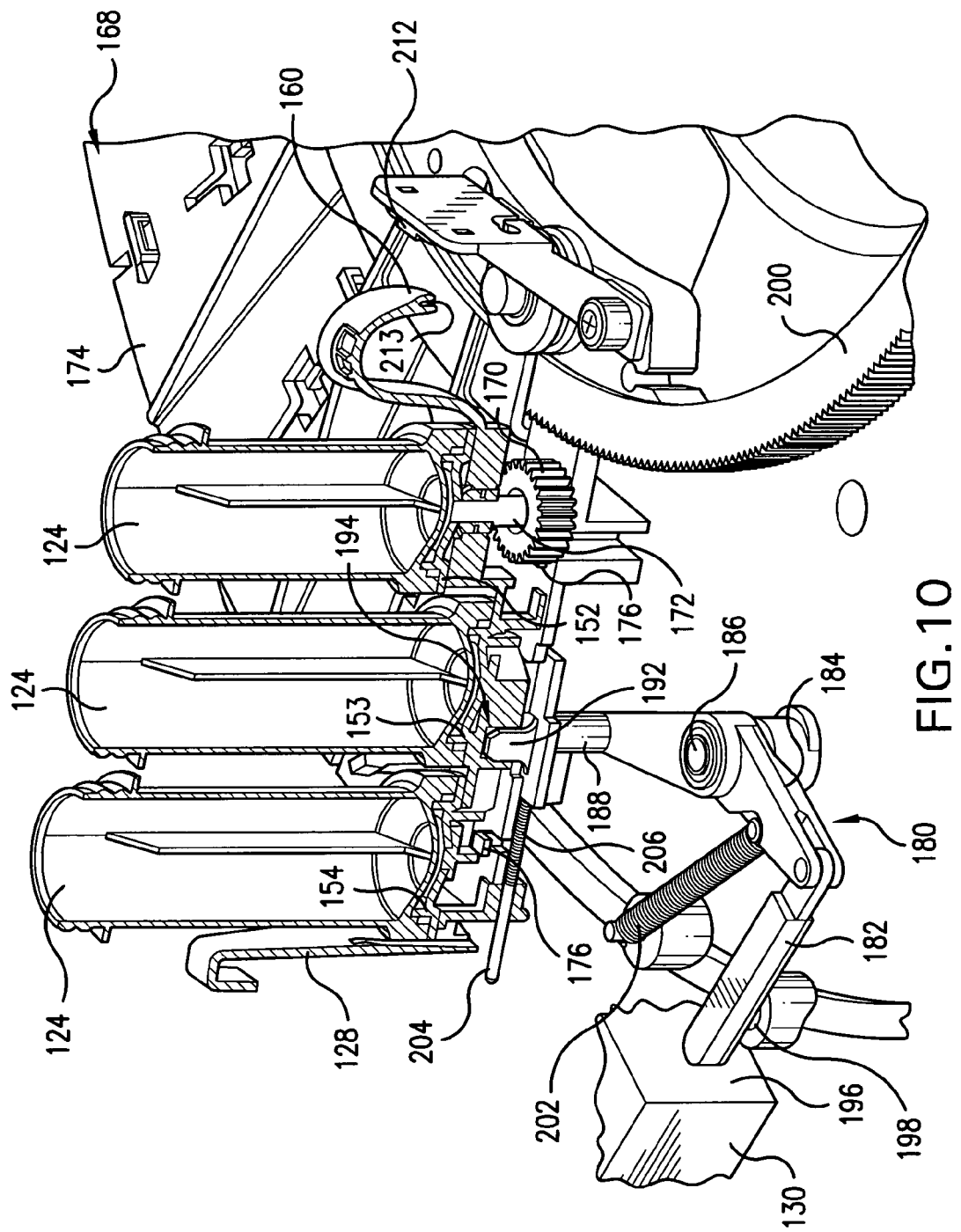
FIGS. 10 and 11 are top and bottom perspective views, respectively, of a reagent positioning and locking system of the embodiment of FIG. 7 in an unlocked position, with a carousel shown in FIG. 10 in cross-section but hidden from FIG. 11 for clarity.

An engagement portion, such as gear 170, is coupled or otherwise associated with holding portion 152, such that the gear 170 is drivable by a member external to the carrier body 150 to rotate holding portion 152. Preferably, the gear 170 is connected by a shaft 172 to the rotatable holding portion 152, as shown in FIG. 10. In an alternative embodiment, a different type of engagement portion can be used, or an on-board drive, such as a motor, can be mounted to the reagent carrier body 150. Although in the preferred embodiment, only one of the holding portions is rotatable or movable with respect to the carrier 128 for producing the stirring in the reagent containers 124, in other embodiments, more than one of the holding portions can be rotatable and more than one can be associated with the gear 170 for driving the motion relative to the carrier body.

The gear 170 preferably is disposed near one end of the carrier body 150, preferably opposite from transporter coupling 162, described below. The gear 170 preferably is exposed on a lower side of the carrier body 150, on an opposite side from the part of the holding portions that are configured for connecting to the containers 124. Holding portion 152 can be elevated with respect to holding portions 153, 154, and preferably accommodates a container 124 that is shorter than the containers 124 placed on the other holding portions 153, 154, preferably to position the upper ends of the containers 124 at substantially the same height.

One end of the carrier body 150 includes a handle portion 160 to facilitate grasping or holding of the loaded carrier by hand by a user. The handle portion 150 preferably is configured as a curved inverted hook with a space large enough to comfortably receive at least one figure of the user. Preferably at the opposite end of the carrier body 150 from the handle portion 160, a transporter coupling 162 is provided, which is preferably similar to a transporter coupling 145 of the sample carrier 126 shown in FIG. 8. The transporter coupling 162 of the preferred embodiment includes an angular hook portion that the transporter is capable of coupling to for lifting, maneuvering, and transporting the carrier to different parts of the diagnostic system.

Figure 14:
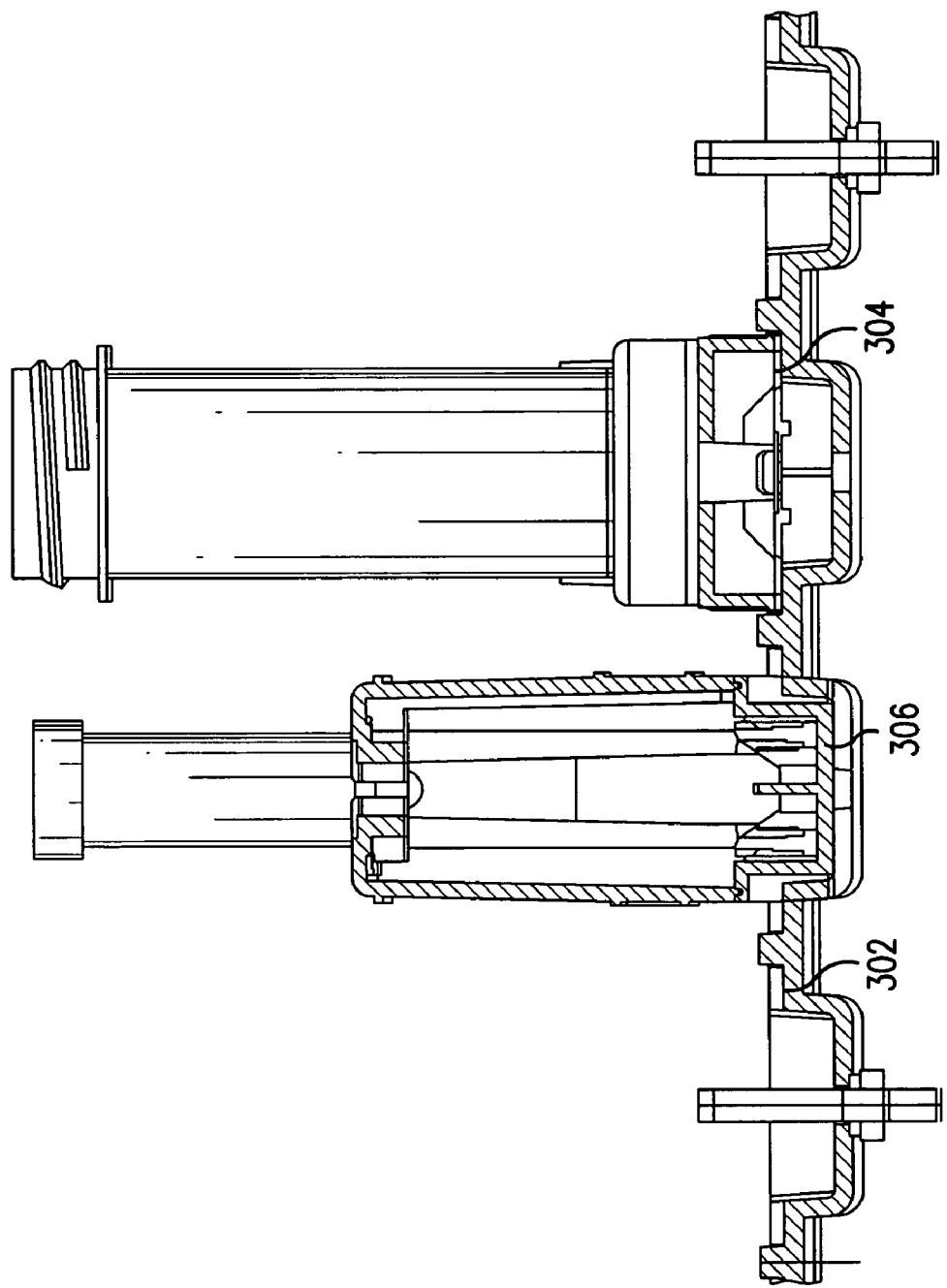
FIG. 14 is a front view of another preferred embodiment of a loading rack

The preferred reagent carrier 128 additionally has an identifying feature, such as a bar code 164. The identifying feature can be a one- or two-dimensional bar code, such as a Code 128 type barcode, or other feature that can be identified by the system. Referring again to FIG. 7, the system includes an identification device which can have a bar code reader 166 or other identification device adapted to interpret and identify information of an identifying feature on the carriers 126 and/or the containers 124. In another embodiment, the identifying feature is disposed on the containers 124, and can by accessed or read by the identification device when the containers 124 are loaded on the carrier 128. In yet another embodiment, the identification device is associated with the transporter 130 such that an action of the transporter 130 can identify the type of contents in the containers 124 on each carrier 128. For instance, the transporter 130 can be provided with a sensor mounted thereon that can sense an identifying feature on the carriers 128 or containers 124. Alternatively, to provide an initial identification of the type of contents, the transporter can sense the physical dimensions of the carriers it is picking up. For instance, the vertical height of the reagent carriers 128 or a portion thereof can be different than the height of the sample carriers 126. In one embodiment the height at which the sample and regent containers are held in the carriers in the loading bay is different and sensed by the identification device to initially determine whether the contents are reagents or samples. As shown in FIG. 14, loading tray pockets 302 catch the wider reagent container base 304, but do not catch the narrower sample carrier base 306. Thus, the reagent container is positioned higher than the sample carrier within the loading tray. The height at which the transporter 130 contacts or engages to lift the respective carrier 126,128 is used by the controlling computer to identify the contents as samples or reagents. In one embodiment, an initial determination of the type of contents is made, such as by determining the height of the carrier transported, and an additional positive and individual identification is made of the contents subsequently, such as by the barcode reader.

In the preferred embodiment, the bar code reader used can read both one- and two-dimensional bar codes, as one-dimensional bar codes are preferably used on the sample containers, while two-dimensional bar codes are used on the reagent carriers. As discussed above, other types of identifying features can be used, and the reagent containers 124 and sample carriers 126 can additionally be labeled with identifying features.

Figure 11:
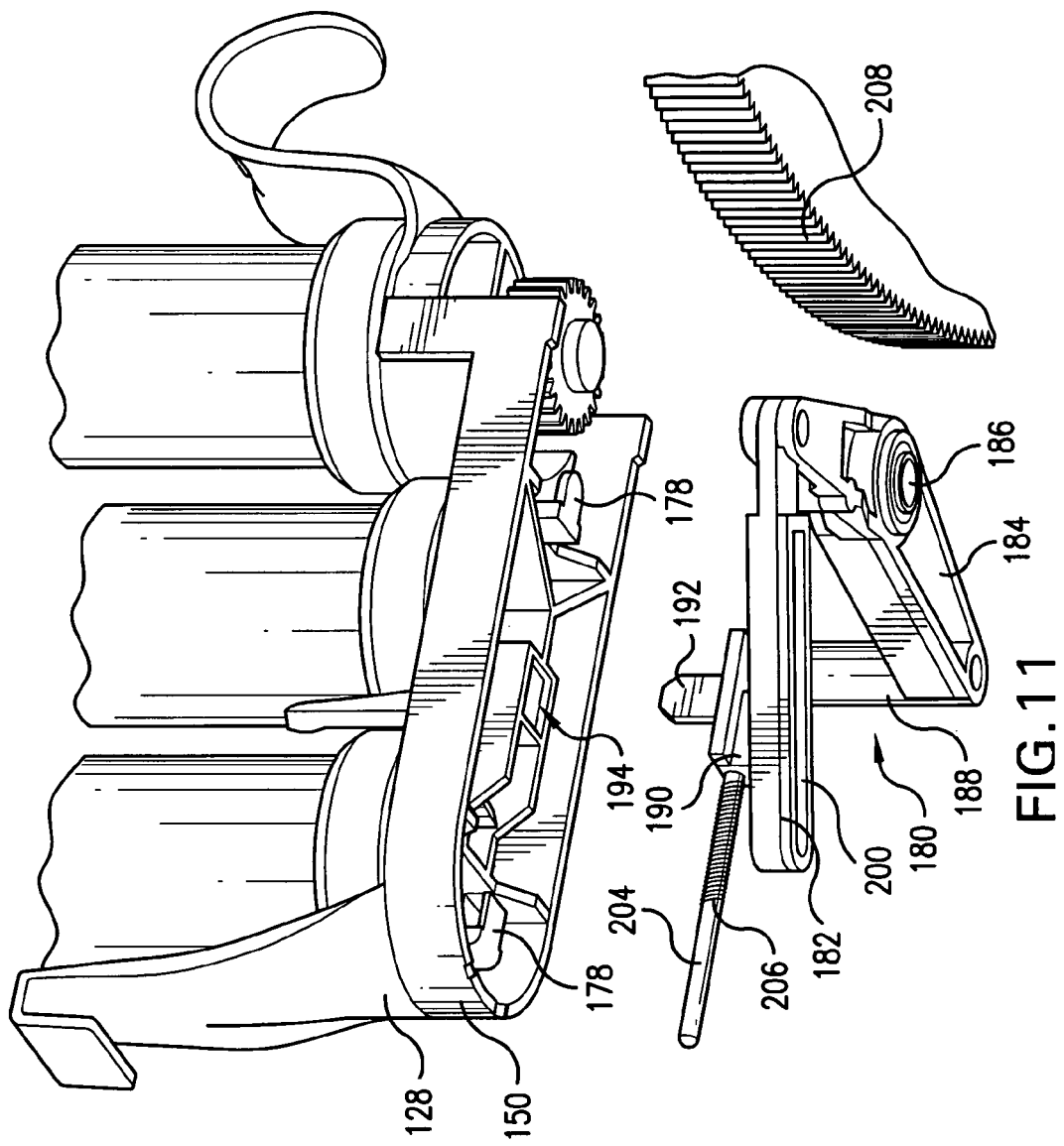

When the transporter 130 is directed by the controlling computer to pick up a carrier 126, 128, it positions the carrier 126,128 for scanning by the bar code reader 166. This enables the system to determine the type of contents that are carried on the carrier. If the system determines that the transported carrier is a sample carrier 126, then the transporter 130 will position the carrier 126 in the appropriate location on the aspiration tray shelf 132. On the other hand, if the system determines that a reagent carrier 128 is being transported, than that carrier 128 can be positioned in a reagent positioning area. The preferred reagent positioning area includes a carousel 168, which is configured to move and preferably rotate about its axis to position the reagents thereon in a location in which they can be accessed when needed by the pipetter 134. The carousel 168 of the preferred embodiment has one or more platforms 174 that form bays in which the reagent carriers 128 are received, as shown in FIG. 10. Retention members, which include a first portion associated with the bays, are configured for locking the carriers 128 to the carousel 168 and releasing them for the transporter 130 to retrieve and transport the carriers 128 to a different location in the device when they are no longer needed on the carousel 168 such as when the reagents thereon have been used up. The portion of the retention member that is disposed on the carousel 168 preferably comprises fixed stirrups 176 that form a loop with an opening extending radially therethrough with respect to the carousel 168. Stirrups 176 are positioned in dimensions to correspond with feet 178 of a second portion of the retaining member, which are associated with the carrier body 150 and feet 178, preferably extending downwardly from the body 150, as shown in FIG. 11. The feet 178 of the preferred embodiment preferably extend downwardly no further than the remaining lowest portion of the carrier 128, which in the preferred embodiment is the lowest portion of the carrier body 150. This enables the carrier 128 to be placed in a flat surface when not being used in the device.

The transporter 130 is operated to lower the carriers 128 onto the carousel 168, preferably with the feet 178 radially aligned with the stirrups 176. When the carrier 128 is slid radially towards the axis of the carousel 168, the feet are received within the opening in the stirrups 176 in an association such that the stirrups 176 retain the feet 178 against axial or upward removal from the carousel 168. Together, the feet 178 and stirrups 176 comprise latchable portions that latch together to assist in substantially locking the carrier 128 to the carousel 168.

Referring to FIGS. 10–13, an activation member 180 is positioned and configured adjacent the carousel 168 for operation by the transporter 130 to control the retention members. In the preferred embodiment, the activation member 180 includes a bar 182 that is accessible by the transporter 130, such that when the transporter 130 moves adjacent the carousel 168, the bar 182 is depressed into the carousel 168. Bar 182 is preferably pivotably attached to a lever 184 that is pivotable about axis 186. At the other end of the lever 184 is a rod 188 that preferably protrudes generally axially for contacting a locking member 190. The activation member 180 and the locking member 190 are preferably disposed beneath the carousel 168 on a side opposite from the carrier 128.

As shown in FIG. 10, when the transporter 130 moves towards the carousel 168, a surface 196 of the transporter 130 presses against bar 182, which causes the lever 184 to pivot about axis 186. The bar 182 is guided by a pin 198 that is received in an elongated groove 200 of the bar 182 on its lower side. When the lever 184 pivots, the rod 188 displaces the locking member 190 radially away from the axis of the carousel 168.

The locking member 190 preferably has a tab 192 that extends upwardly through the platforms 174 and protrudes on the upper side of the carousel 168. The transporter 130 lowers the carrier 128 so that the tab 192 is received in an opening 194 of the carrier 128. With the carrier 128 seated on the carousel 168 and the tab 192 received in the opening 194, the transporter 130 moves away from the carousel to perform another transporting operation on a different carrier 126,128. When this happens, spring 202 resiliently biases the lever 180 to a position permitting the locking of the carrier 128 to the carousel. Additionally, the locking member 190 has a guide shaft 204 about which is mounted a spring 206. When rod 188 moves radially towards the axis of the carousel 168, spring 202 resiliently returns the lever 184 to its original position, and tab 192 displaces the carrier 128 along the platform 174, thus also displacing the feet 178 towards the axis of the carousel 168. This motion causes the feet 178 to latchedly enter the stirrups 176, and together with the locking tab 194, substantially lock the carrier 128 to the carousel 168.

In the preferred embodiment, the physical contact of the transporter 130 against the activation member mechanically displaces and operates the activation member to lock or unlock the carrier 128 to or from the carousel 168. In another embodiment, the contact between the transporter 130 and the activation member can cause an electrically or otherwise driven mechanism to lock or unlock the carrier. In one embodiment, a solenoid or motor operates the locking member, and this can be completely controlled by the controlling computer, without directly being activated by any physical contact from the transporter 130.

Figure 12:
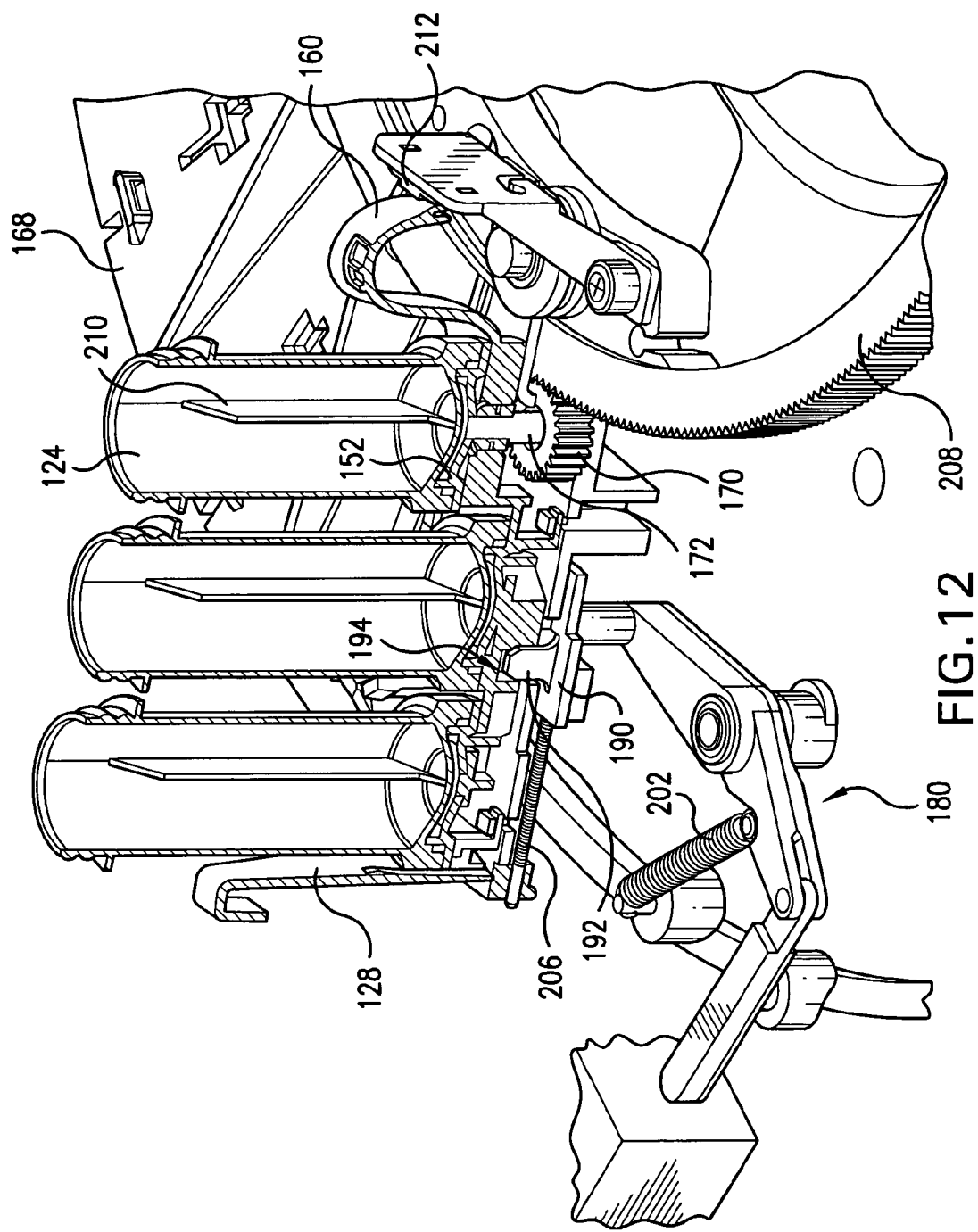
FIGS. 12 and 13 are top and bottom perspective views, respectively, of the reagent carrier in a locked position.
Figure 13:
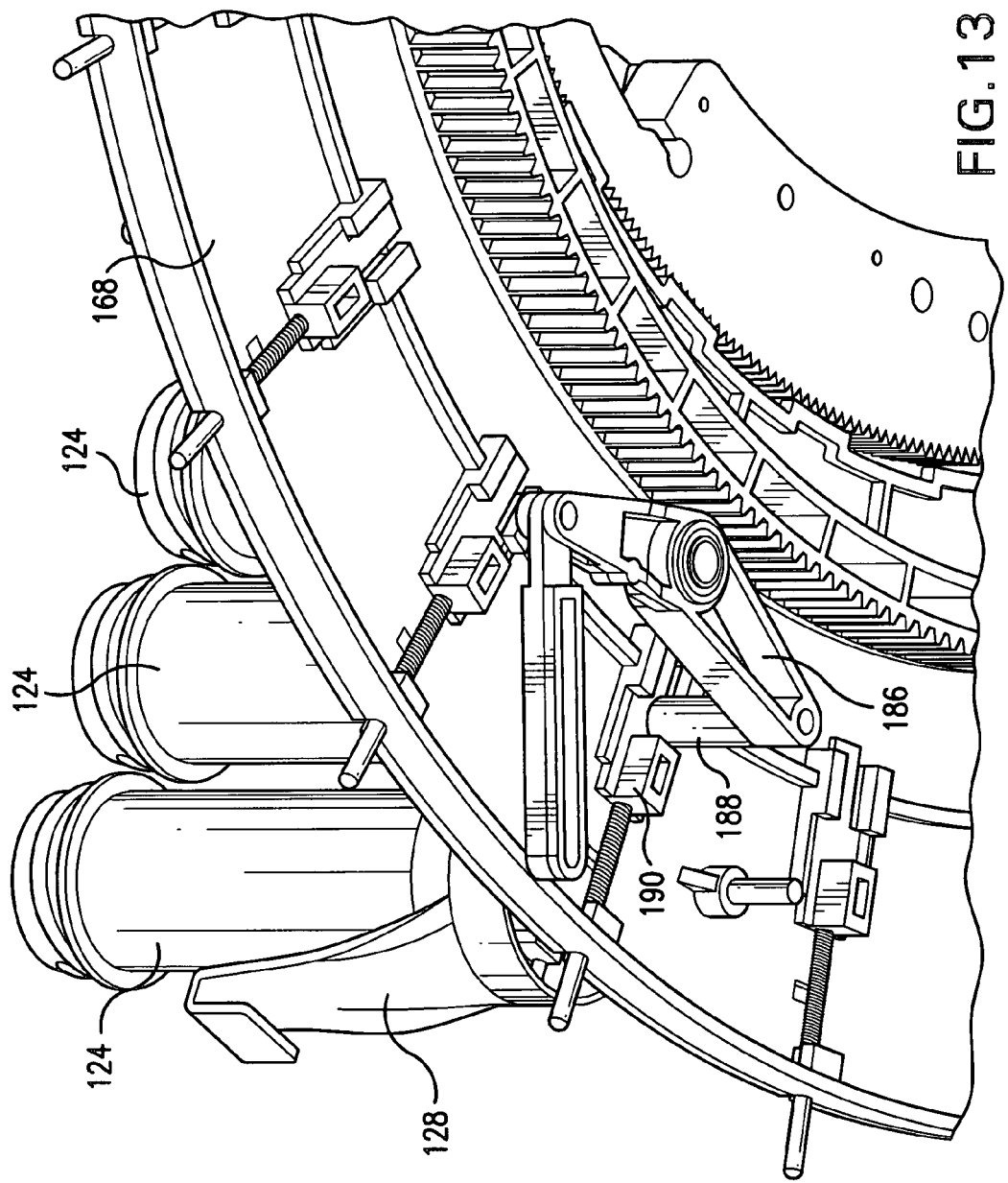

The same motion of the carrier 128 towards the locked position caused by the locking member 190 preferably also meshes gear 170 with an engagement portion that is associated with the carousel 168. This engagement portion is preferably associated with the carousel 168, and in the preferred embodiment comprises a ring gear 208 that is preferably stationary. With the gear 170 and ring gear 208 meshed, rotation of the carousel 168 about the ring gear 208 spins both the gear 170 and the container 124 mounted to holding portion 152. As seen in FIG. 12, the preferred container 124 includes internal ribs 210, which improve stirring and mixing of the contents therein.

The actuation portion 180 is preferably mounted to a stationary portion of the device that does not rotate with the carousel 168. The locking members 190 and the rod 188 are resiliently biased by springs 202,206 to positions so that rod 188 is aligned with gaps adjacent the locking members, which are aligned circumferentially along the carousel 168. Thus, as the carousel 168 rotates, the rod 188 passes adjacent to the locking members 190, preferably without coming in contact therewith, and substantially without interfering with or causing the locking members 190 to move from their locked positions.

As shown in FIGS. 10 and 12, a carrier sensor 212 is preferably mounted on a fixed portion in the interior of the carousel 168. The carrier sensor 212 is configured for detecting the presence of a carrier 128 on the carousel 168 or a carrier 128 in the locked position on the carousel 168. The preferred carrier sensor 212 is a Hall effect sensor that is configured to detect the presence of a magnet 213 embedded in the handle portion 160 of the carrier 128. Alternatively, other kinds of sensors can be used, such as a capacitive sensor to directly detect the presence of the carrier material, which is preferably plastic. The sensor 212 preferably transmits a signal to the controlling computer to indicate the presence or absence of the carrier 128 in the locked position on the carousel 168 at the loading location, where the transporter 130 can load the reagent carrier 128 onto the carousel 168.

In the operation of the device, the controlling computer keeps track of the position on the carousels 128 holding each reagent in the reagent containers 124. The pipetter 134 preferably has a pivoting arm 214 that can pivot along an arc 216. The rotational position of the carousel 168 and the pivoting arm 214 are controlled by the controlling computer to intersect the selected reagent container with the locus of the pipetter 134. Thus, the pipetter can draw the desired amount of reagent to transmit it to a diagnostic testing area 218 of the diagnostic module. The pivoting arm 214 is also movable to position the pipetter over the sample container 122 from which a sample is to be drawn, and the drawn sample can also be delivered to a diagnostic testing area 218.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. For example, reagent positioning devices other then carousels can be used for positioning the reagents and desired location for access by the pipetter, and the ring gear that drives the gear on the carrier to rotate one of the holders can also be driven to rotate without requiring any motion from the carousel to mix the microparticles or any other substance in the storage container.

What is claimed is:

1. An assay testing diagnostic analyzer system, comprising:
   a loading bay for loading a plurality of carriers that are configured for holding containers that contain fluid substances for use in a diagnostic process;
   a positioning device configured for receiving and positioning the carriers for access by a diagnostic module to perform the diagnostic process;
   a transporter configured for transporting the carriers from the loading bay to the positioning device;
   a retention member associated with the positioning device and configured for locking the carriers to the positioning device, the retention member being operatively associated with the transporter for releasing the carriers therefrom to enable the transporter to transport the carrier from the positioning device, further comprising an activation member operably associated with the transporter for releasing at least one of the carriers when the transporter is in contact with the activation member.

2. The diagnostic system of claim 1, wherein the positioning device is driven to position the carriers for access by the diagnostic module.

3. The diagnostic system of claim 2, wherein the positioning device comprises a rotating carousel.

4. The diagnostic system of claim 1, further comprising the diagnostic module, which is configured for performing the diagnostic process by accessing and combining the substances from one of the containers and also another substance to perform the diagnostic process.

5. The diagnostic system of claim 4, wherein the substance in the container comprises a reagent, and the other substance comprises a sample.

6. The diagnostic system of claim 1, further comprising a carrier locking member configured for moving with respect to the positioning device in association with the carrier for locking and unlocking the carrier with respect to the positioning device, the activation member being configured for being displaced by the transporter to move the locking member for the locking and unlocking of the carrier.

7. The diagnostic system of claim 1, wherein the retention member comprises first latching member configured for lockingly latching to a second latching member of at least one of the carriers for locking the carrier to the positioning device, the retention member being configured for relatively moving the latching members for locking and unlocking the carrier.

8. The diagnostic system of claim 7, further comprising a locking member movable with respect to the positioning device and associated with the carrier for moving the second latching member with respect to the first latching member for locking and unlocking the carrier.

9. The diagnostic system of claim 8, further comprising an activation member operatively associated with the transporter for releasing the carrier when the transporter is in contact with the activation member, the locking member comprising a tab that is received in a recess of the carrier and which is configured for sliding the carrier with respect to the latching member.

10. The diagnostic system of claim 1, further comprising:
the plurality of carriers;
a plurality of the retention members;
a carrier sensor configured for detecting the presence of the carriers on the positioning device.

11. The diagnostic system of claim 10, wherein the carriers have an identifying feature, the diagnostic system further comprising:
an identification device configured for identifying the identifying feature of the carriers; and
a programmable computer for controlling the movement of the transporter and the positioning device based on input data and a preprogrammed priority order for processing a the contents of the carriers based on the identified identifying feature.

* * * * *